US009890180B2

(12) United States Patent
Cantat et al.

(10) Patent No.: US 9,890,180 B2
(45) Date of Patent: Feb. 13, 2018

(54) METHOD FOR PREPARING OXYBORANE COMPOUNDS

(71) Applicant: Commissariat A L'Energie Atomique Et Aux Energies Alternatives, Paris (FR)

(72) Inventors: Thibault Cantat, Issy les Moulineaux (FR); Christophe Gomes, Antony (FR); Enguerrand Blondiaux, Orsay (FR); Olivier Jacquet, Orsay (FR)

(73) Assignee: Comissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/781,506

(22) PCT Filed: Apr. 1, 2014

(86) PCT No.: PCT/IB2014/060356
§ 371 (c)(1),
(2) Date: Sep. 30, 2015

(87) PCT Pub. No.: WO2014/162266
PCT Pub. Date: Oct. 9, 2014

(65) Prior Publication Data
US 2016/0052943 A1    Feb. 25, 2016

(30) Foreign Application Priority Data
Apr. 3, 2013   (FR) .................................. 13 52996

(51) Int. Cl.
*C07F 5/02*       (2006.01)
*C07C 29/09*      (2006.01)
*G01N 33/60*      (2006.01)

(52) U.S. Cl.
CPC ............. *C07F 5/027* (2013.01); *C07C 29/09* (2013.01); *C07F 5/02* (2013.01); *C07F 5/025* (2013.01); *G01N 33/60* (2013.01)

(58) Field of Classification Search
CPC .. C07F 5/027; C07F 5/025; C07F 5/02; C07C 29/09; G01N 33/60
USPC ................................................ 568/3, 6, 840
See application file for complete search history.

(56) References Cited

PUBLICATIONS

Chakraborty et al. Catalytic properties of nickel bis(phosphinite) pincer complexes in the reduction of CO2 to methanol derivatives. Polyhedron 32 (2012) 30-34. Available online May 4, 2011.*
Sgro et al. Frustrated Lewis Pair Inspired Carbon Dioxide Reduction by a Ruthenium Tris(aminophosphine) Complex. Angew. Chem. Int. Ed. 2012, 51, 11343-11345 and supplemental information.. Published online: Oct. 4, 2012.*
Pubill-Ulldemolins et al. Essential role of phosphines in organocatalytic β-boration reaction†. Org. Biomol. Chem., 2012, 10, 9677-9682 and supplemental information. Published on Oct. 25, 2012.*
International Search Report and Written Opinion for corresponding International Patent Application No. PCT/IB2014/060356 dated Jun. 5, 2014.
Huang, Fang et al.; "How Does the Nickel Pincer Complex Catalyze the Conversion of Co2 to a Methanol Derivative? A Computational Mechanistic Study"; Inorganic Chemistry; vol. 50, No. 8; Apr. 18, 2011; pp. 3816-3825; XP055081618.
Menard, Gabriel et al.; "Room Temperature Reduction of Co2 to Methanol by Al-Based Frustrated Lewis Pairs and Ammonia Borane"; Journal of the American Chemical Society; vol. 132, No. 6; Feb. 17, 2010; pp. 1796-1797; XP055081620.
Bontemps, Sebastien et al.; "Borane-Mediated Carbon Dioxide Reduction at Ruthenium: Formation of C1 and C2 Compounds"; Angewandte Chemie International Edition; vol. 51, No. 7; Feb. 13, 2012; pp. 1671-1674; XP055081601.
Chakraborty, Sumit et al.; "An Efficient Nickel Catalyst for the Reduction of Carbon Dioxide with a Borane"; Journal of the American Chemical Society; vol. 132, No. 26; Jul. 7, 2010; pp. 8872-8873; XP055081607.
Shintani, Ryo et al.; "Copper-Catalyzed Hydroboration of Carbon Dioxide"; Organmetallics; vol. 32, No. 8; Apr. 3, 2013; pp. 2459-2462; XP055081611.
Benson, E.E. et al.; Chem. Soc. Rev., 2009, 38, 89.
Izumi, Y. et al.; Coord. Chem. Rev., 2013, 257, 171.
Jessop, P.G. et al.; Chem. Rev., 1995, 95, 259.
Wang, W. et al.; 2011, 3703.
Riduan, S.N., et al.; Angew. Chem. Int. Ed., 2009, 48, 3322.
Berkefeld, A. et al.; J. Am. Chem. Soc., 2010, 132, 10660.
Matsuo, T. et al.; J. Am. Chem. Soc., 2006, 128.
Chakraborty, Y. et al.; Polyhedron, 2012, 32, 30.
Chakraborty, Y. et al.; Inorg. Chem., 2013, 52, 37.
Srgo, M.J. et al.; Angew. Chem. Int. Ed., 2012, 51, 11343.
Choudhry, S.C. et al.; Journal of Organic Chemistry, 1989, vol. 54, pp. 3755-3757.
Pleiss, U. and Voges, R.; Synthesis and Applications of Isotopically Labelled Compounds; vol. 7, Wiley-VCH, 2001.

(Continued)

*Primary Examiner* — Yih-Horng Shiao
(74) *Attorney, Agent, or Firm* — Alston & Bird LLP

(57) ABSTRACT

A method for preparing oxyborane compounds of formula (I): using carbon dioxide, and the use of the oxyborane compounds obtained in this way for preparing methane derivatives, in particular oxygenated, halogenated or amino derivatives of methane. The methane derivatives obtained in this way can then be used in the production of vitamins, pharmaceutical products, glues, acrylic fibers and synthetic leathers, pesticides, and fertilizers, for example. Also provided is a method for producing vitamins, pharmaceutical products, glues, acrylic fibers, synthetic leathers, pesticides, and fertilizers, for example, including a step of preparing methane derivatives, in particular oxygenated, halogenated or amino derivatives of methane, from oxyborane compounds obtained by the method according to the invention. Further provided is a method of preparing labelled oxyborane compounds and the use of same.

22 Claims, No Drawings

(56) References Cited

PUBLICATIONS

Voges, R. et al.; Preparation of Compounds Labeled with Tritrium and Carbon-14, Wiley-VCH: Chippenham (UK) 2009.
Wei, C.S. et al.; J. Am. Chem. Soc., 2010, 132, 3078.
Wu, J.Y. et al.; J. Am. Chem. Soc. 2009, 131, 12915.
Farrell, J.M. et al.; J. Am. Chem. Soc., 2012, 134, 15728.
Brown, J.M. et al.; J. Am. Chem. Soc., 1994, 116, 866.
Segawa, Y. et al.; J. Am. Chem. Soc., 2008, 130, 16069.
Lu, Z.P. et al.; Angew. Chem. Int. Ed., 2011, 50, 12227.
Kochina, T.A., et al.; J. Gen. Chem., 2002, 72, 1222.
Shishigin, E.A. et al.; Russ. J. Gen. Chem., 2005, 75, 152.

* cited by examiner

METHOD FOR PREPARING OXYBORANE COMPOUNDS

FIELD

The present invention relates to a process for the preparation of oxyborane compounds using carbon dioxide and to the use of the oxyborane compounds thus obtained in the preparation of methane derivatives, in particular oxygen-comprising, halogen-comprising or amine-comprising methane derivatives. The methane derivatives thus obtained can then be used in the manufacture of vitamins, pharmaceutical products, adhesives, acrylic fibers and synthetic leathers, pesticides and fertilizers, for example.

The invention also relates to a process for the manufacture of vitamins, pharmaceutical products, adhesives, acrylic fibers, synthetic leathers, pesticides and fertilizers, for example, comprising a stage of preparation of the methane derivatives, in particular oxygen-comprising, halogen-comprising or amine-comprising methane derivatives, from oxyborane compounds obtained by the process according to the invention.

In addition, the present invention relates to a process for the preparation of labelled oxyborane compounds and to their uses.

BACKGROUND

The use of $CO_2$ which can be recovered in value as carbon source for the production of chemical consumables is a key challenge in order to decrease its accumulation in the atmosphere but also in order to control our dependence on fossil fuels.

The greatest challenge faced by scientists and manufacturers is that of recycling $CO_2$, that is to say of developing reactions which make it possible to produce chemical compounds, such as, for example, fuels, plastic polymers, medicaments, detergents or high-tonnage molecules traditionally obtained by petrochemical methods. The technical difficulty lies in the development of chemical reactions which make it possible to functionalize $CO_2$ while reducing the central carbon (i.e., while replacing the C—O bonds of the $CO_2$ with C—H or C—C bonds).

The catalytic reduction of $CO_2$ to give formic acid HCOOH, formaldehyde $H_2CO$, methanol $CH_3OH$ and methane $CH_4$ is arousing increasing interest in the search for novel synthetic fuels. In this context, the main reduction processes can be classified according to the nature of the reducing agent used, as shown in sections 1 to 4 below. The use of powerful reducing agents, such as alkali metals (Li, Na, K) or metal hydrides (aluminum hydride, borohydrides, and the like), is ruled out as these reactants result in highly exothermic reactions in the presence of $CO_2$ and thus do not make it possible to provide a favorable energy balance in the reduction of carbon dioxide.

1. Electrochemical and Photoelectrochemical Methods

The use of electrons provided by an electrolysis assembly in order to reduce $CO_2$ remains a highly dynamic field of research which is motivated by the hope of finding efficient and selective catalysts which make it possible, for example, to selectively reduce $CO_2$ in the presence of protons while avoiding the formation of molecular hydrogen $H_2$ (E. E. Benson, C. P. Kubiak, A. J. Sathrum and J. M. Smieja, Chem. Soc. Rev., 2009, 38, 89). Photoelectroreduction processes are also being studied (Y. Izumi, Coord. Chem. Rev., 2013, 257, 171).

2. Hydrogenation of $CO_2$

The reaction between $CO_2$ and molecular hydrogen can result in the formation of formic acid (in the presence of a base), of methanol or of methane. Molecular catalysts (homogeneous catalysts) and heterogeneous catalysts have been described for facilitating this reaction (P. G. Jessop, T. Ikariya and R. Noyori, Chem. Rev., 1995, 95, 259; W. Wang, S. Wang and J. Gong, 2011, 3703).

3. Hydrosilylation of $CO_2$

The reaction between $CO_2$ and hydrosilanes (characterized by the presence of an Si—H bond) makes it possible to reduce $CO_2$ to give formoxysilane, bis(silyl)acetals and methoxysilanes which can result, after hydrolysis, in formic acid HCOOH, in formaldehyde $H_2CO$ and in methanol $CH_3OH$ respectively (S. N. Riduan, Y. G. Zhang and J. Y. Ying, Angew. Chem. Int. Ed., 2009, 48, 3322; A. Berkefeld, W. E. Piers and M. Parvez, J. Am. Chem. Soc., 2010, 132, 10660). Some catalysts also make it possible to directly reduce $CO_2$ to methane (T. Matsuo and H. Kawaguchi, J. Am. Chem. Soc., 2006, 128). In these reactions, siloxanes and silanols are formed as by-products.

4. Hydroboration of $CO_2$

The reaction between $CO_2$ and a hydroborane of formula (I) is referred to as hydroboration reaction of $CO_2$. This conversion requires the use of a catalyst. Three different catalytic systems are known to date. They are described in detail below.

The group of Hairong Guan (University of Cincinnati, USA) developed the first catalyst for the hydroboration of $CO_2$ in 2010 (S. Chakraborty, J. Zhang, J. A. Krause and H. R. Guan, J. Am. Chem. Soc., 2010, 132, 8872; S. Chakraborty, Y. J. Patel, J. A. Krause and H. R. Guan, Polyhedron, 2012, 32, 30; S. Chakraborty, J. Zhang, Y. J. Patel, J. A. Krause and H. R. Guan, Inorg. Chem., 2013, 52, 37). It is a nickel complex which makes it possible to carry out the reduction of $CO_2$ to give methoxyborane. Formoxyborane is observed as reaction intermediate. The hydroboranes used are catecholborane (catBH), 9-borabicyclo[3.3.1]nonane (9-BBN) and pinacolborane (pinBH). The catalyst operates at ambient temperature in the presence of 1 bar of $CO_2$. With catecholborane, the Turn-Over Number (TON, defined below) of the catalyst is 495 at 25° C. and its Turn-Over Frequency (TOF, defined below) is 495 h$^{-1}$. This reaction is shown in scheme 1 below.

Scheme 1

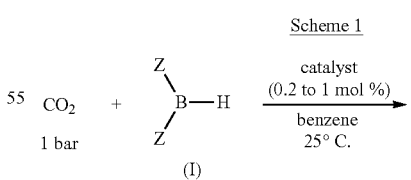

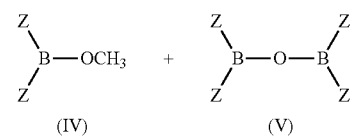

-continued

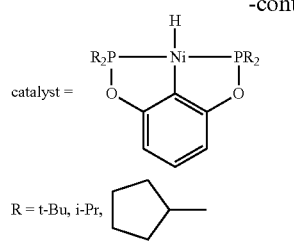

catalyst =

R = t-Bu, i-Pr, cyclopentyl for R = t-Bu:
TON = 495
TOF = 485 h$^{-1}$
at 25° C. with catecholborane

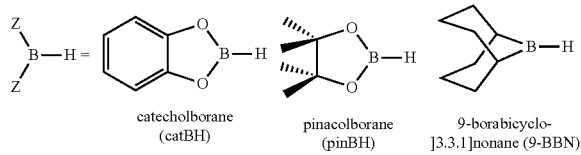

catecholborane (catBH)   pinacolborane (pinBH)   9-borabicyclo-[3.3.1]nonane (9-BBN)

In the scheme above and in the continuation of the account, TON and TOF are defined as follows:

$$TON = \frac{\text{amount of borane } (R^1R^2BH) \text{ at the end of the reaction}}{\text{amount of borane } (R^1R^2BH) \text{ at the start of the reaction}} \times \frac{100}{\text{catalytic charge in mol\%}}$$

$$TOF = \frac{\text{amount of borane at the end of the reaction}}{\text{amount of borane at the start of the reaction}} \times \frac{100}{\text{catalytic charge in mol\%}} \times \frac{1}{\text{reaction time in hours}}$$

Thus, the higher TON and TOF, the more effective the catalyst.

In 2012, the group of Sylviane Sabo-Etienne (CNRS, Toulouse, France) described a catalyst based on a ruthenium hydride complex for the hydroboration reaction of $CO_2$ (S. Bontemps, L. Vendier and S. Sabo-Etienne, *Angew. Chem. Int. Ed.*, 2012, 51, 1671). The authors showed that the hydroboration reaction of $CO_2$ could result in intermediates of bis(boryl) acetal and boroxymethyl formate ($R^1R^2B$—$OCH_2OCHO$) types. These intermediates were not isolated.

Only pinacolborane was used and a high catalyst charge was used (10 mol %). Under these conditions, the activity of the catalyst is low and the formation of methoxyborane requires 22 days of reaction at ambient temperature or 5 h at 70° C. This reaction is shown in scheme 2 below.

Scheme 2

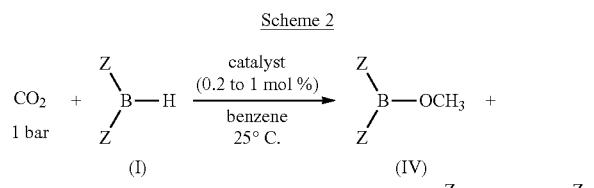

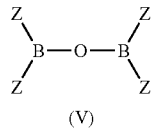

catalyst =
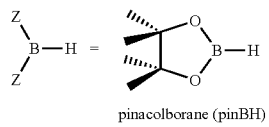
TON = 10
TOF = 2 h$^{-1}$
at 70° C. with pinacolborane pinacolborane (pinBH)

In 2012, the group of Douglas W. Stephan (University of Toronto, Canada) described a ruthenium-based catalyst for the hydroboration of $CO_2$ (M. J. Sgro and D. W. Stephan, *Angew. Chem. Int. Ed.*, 2012, 51, 11343). Catecholborane and 9-borabicyclo[3.3.1]nonane were used as reactants. They did not show a difference in reactivity. The reaction is slow at 50° C. with a catalyst load of 1.0 mol %. This reaction is shown in scheme 3 below.

Scheme 3

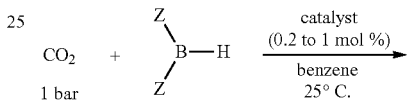

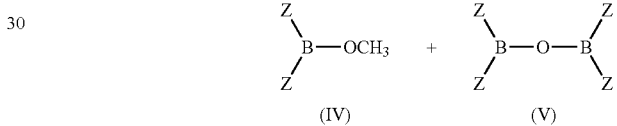

catalyst =
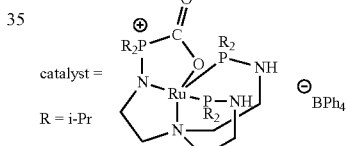
R = i-Pr

TON = 27
TOF = 0.28 h$^{-1}$
at 25° C. with catecholborane

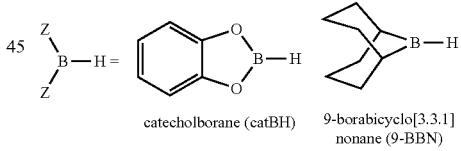

catecholborane (catBH)   9-borabicyclo[3.3.1]nonane (9-BBN)

Conversions involving reaction promoters (such as $Mes_3P/AlCl_3$ or $Mes_3P/AlBr_3$ (Mes=mesityl) mixtures) in stoichiometric amounts, that is to say, non-catalytic amounts, have also been described by G. Ménard and D. W. Stephan, *J. Am. Chem. Soc.*, 2010, 132, 1796.

The conversion of $CO_2$ to chemical consumables, such as, for example, methane derivatives, in particular oxygen-comprising, halogen-comprising or amine-comprising methane derivatives, especially formic acid, formaldehyde and methanol, methane, methyl halide and methyl amine, by a hydroboration reaction of $CO_2$ is arousing increasing interest. The reaction of $CO_2$ with a hydroborane, which takes place in two stages, results in advantageous synthetic intermediates of formoxyborane ($R^1R^2BO$—CHO), methoxyborane ($R^1R^2B$—O—$CH_3$) or bis(boryl) acetal (($R^1R^2B$—O)$_2CH_2$) type. These intermediates, which can also be more generally denoted as "oxyborane compounds" as a result of the presence of "R¹R²B—O—" in these compounds, are stable and readily lend themselves to various types of reactions in order to result in varied chemical compounds, such as formic acid, formaldehyde, methanol, methane, methyl halide, methyl amine, and the like.

However, due to the high thermodynamic stability of carbon dioxide, its conversion into oxyborane compounds necessarily has to involve effective catalysts so as to promote the thermodynamic balance of this chemical conversion.

Furthermore, the hydroboration reaction requires the use of an effective catalyst as, in its absence, the product resulting from this chemical conversion cannot be obtained in a measurable fashion in a short period of time (less than one week) and at a temperature of less than 150° C.

In point of fact, to date, hydroboration reactions of $CO_2$ deploy a limited number of catalysts which, moreover, are essentially complexes of transition metals which are often expensive and/or toxic, such as nickel or ruthenium.

In the context of the conversion of $CO_2$ by a hydroboration reaction, first into "oxyborane compounds" and then into chemical consumables, such as, for example, methane derivatives, in particular oxygen-comprising, halogen-comprising or amine-comprising methane derivatives, especially formic acid, formaldehyde, methanol, methane, methyl halide and methyl amine, the technical challenge to be taken up is that of developing effective catalysts which overcome the problems of toxicity and of costs generally associated with the use of known metal catalysts, in particular catalysts based on precious metals.

There thus exists a real need for a catalyst which makes possible the conversion of $CO_2$ and a hydroborane into oxyborane compounds, by a hydroboration reaction, which is effective (capable of increasing the rate of the conversion of the $CO_2$ even in a low amount), selective (promoting the production of the desired product in comparison with the by-products) and not very expensive and/or not very toxic compared with the catalysts known for the conversion of $CO_2$ into oxyborane compounds by this type of reaction.

In particular, there exists a real need for a catalyst, as defined above, which does not comprise:
  alkaline earth metals from Group IIA of the Periodic Table of the Elements (such as magnesium and calcium);
  transition metals from Group IB to VIIIB of the Periodic Table of the Elements (such as nickel, iron, cobalt, zinc, copper, rhodium, ruthenium, platinum, palladium or iridium);
  rare earth metals, the atomic number of which is between 57 and 71 (such as lanthanum, cerium, praseodymium or neodymium); or
  actinides, the atomic number of which is between 89 and 103 (such as thorium or uranium).

Furthermore, oxyborane compounds incorporating radioisotopes and/or stable isotopes and capable of being converted into different labelled chemical compounds, such as formic acid, formaldehyde, methanol, methane, methyl halide, methyl amine, and the like, are of particular interest in many fields, such as, for example, in life sciences (study/elucidation of enzymatic mechanisms or of biosynthetic mechanisms, in biochemistry, and the like), environmental sciences (tracing of wastes, and the like), research (study/elucidation of reaction mechanisms) or the research and development of novel pharmaceutical and therapeutic products. Thus, to develop a process for the preparation of labelled oxyborane compounds meeting the requirements indicated above can meet a real need.

There thus exists a real need to have available a process which makes it possible to prepare labelled oxyborane compounds incorporating radioisotopes and/or stable isotopes starting from labelled reactants, such as, for example, labelled $CO_2$ and/or a labelled hydroborane.

SUMMARY

It is an aim of the present invention to specifically meet these needs by providing a process for the preparation of oxyborane compounds of formula (I):

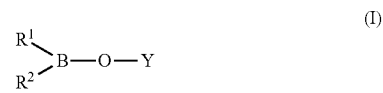

(I)

in which:
  R¹ and R² represent, independently of one another, a hydrogen atom, a halogen atom, an alkyl group, an alkenyl group, an alkynyl group, an aryl group, a heteroaryl group, a heterocycle, a silyl group, a siloxy group, an amino group or an alkoxy group, said alkyl, alkenyl, alkynyl, aryl, heteroaryl, heterocycle, silyl, siloxy, amino and alkoxy groups optionally being substituted, or
  R¹ and R², taken together with the boron atom to which they are bonded, form an optionally substituted heterocycle,
  Y represents —CHO, —CH₂—O—BR¹R², with R¹ and R² as defined above, or —CH₃,
  R¹, R² and Y optionally comprise, independently of one another, an H, C, N, O, F, Si and/or S as defined below:
    H represents a hydrogen atom (¹H), deuterium (²H) or tritium (³H),
    C represents a carbon atom (¹²C) or a ¹¹C, ¹³C or ¹⁴C isotope,
    N represents a nitrogen atom (¹⁴N) or a ¹⁵N isotope,
    O represents an oxygen atom (¹⁶O) or an ¹⁸O isotope,
    F represents a fluorine atom (¹⁹F) or a ¹⁸F isotope,
    Si represents a silicon atom (²⁸Si) or a ²⁹Si or ³⁰Si isotope,
    S represents a sulfur atom (³²S) or a ³³S, ³⁴S or ³⁶S isotope,
characterized in that a hydroborane of formula (II), in which R¹, R² and H are as defined above:

(II)

is reacted with $CO_2$, in which C and O are as defined above, and
in the presence of a catalyst chosen from the group consisting of:
i. organic bases chosen from nitrogen-comprising organic bases, phosphorus-comprising organic bases, carbon-comprising bases or oxygen-comprising organic bases;
ii. organic or inorganic boron compounds; or
iii. organic or inorganic aluminum compounds.

Thus, the process of the invention makes it possible to prepare both unlabelled oxyborane compounds of formula (I) and labelled oxyborane compounds of formula (I).

The process of the invention also has the advantage of making it possible to convert $CO_2$ into oxyborane compounds with a large choice of catalysts. The catalysts used in the process of the invention overcome the problems of toxicity and of costs generally associated with the use of metal catalysts, the metal of which is:

- an alkaline earth metal from Group IIA of the Periodic Table of the Elements (such as magnesium and calcium);
- a transition metal from Group IB to VIIIB of the Periodic Table of the Elements (such as nickel, iron, cobalt, zinc, copper, rhodium, ruthenium, platinum, palladium or iridium);
- a rare earth metal, the atomic number of which is between 57 and 71 (such as lanthanum, cerium, praseodymium or neodymium); or
- an actinide, the atomic number of which is between 89 and 103 (such as thorium or uranium).

Depending on the conditions, the process of the invention, the oxyborane compounds can be obtained in the form of a mixture of compounds of formula (I) or with a good selectivity (which can reach 100% for a single type of oxyborane compound of formula (I)).

The process of the invention can result in the oxyborane compounds of formula (I) with a good, indeed even excellent, yield (ranging from 50% to 100%, for example).

DETAILED DESCRIPTION

In the context of the present invention, the yield is calculated with respect to the amount of hydroborane of formula (II) initially introduced, on the basis of the amount of oxyborane compound of formula (I) isolated:

Yield=$n$(oxyborane)/($n$(oxyborane)+$n$(hydroborane)),
$n$ being the amount of material.

In the context of the present invention, the selectivity relates to the nature of the oxyborane products of formula (I) formed starting from the hydroborane of formula (II).

In order for the process of the invention to be able to result in an oxyborane compound of formula (I) being obtained, a judicious and appropriate combination of hydroboranes of formula (II) and of catalysts is essential. It is in particular necessary for the hydroborane of formula (II) and the catalyst to be chosen by taking into account in particular their respective steric hindrances, the reducing nature of the hydroborane, the nucleophilic nature of the catalyst and their solubility in the reaction medium.

"Alkyl" is understood to mean, within the meaning of the present invention, an optionally substituted, saturated or unsaturated and linear, branched or cyclic carbon-comprising radical comprising from 1 to 12 carbon atoms. Mention may be made, as saturated and linear or branched alkyl, for example, of the methyl, ethyl, propyl, butyl, pentyl, hexyl, octyl, nonyl, decyl, undecyl and dodecanyl radicals and their branched isomers. Mention may be made, as cyclic alkyl, of the cyclopropyl, cyclobutyl, cyclopentyl, cyclohexyl, bicyclo[2.1.1]hexyl and bicyclo[2.2.1]-heptyl radicals. Mention may be made, as unsaturated cyclic alkyls, for example, of cyclopentenyl or cyclohexenyl. The unsaturated alkyls, also known as "alkenyl" or "alkynyl", respectively comprise at least one double bond or one triple bond. Mention may be made, as such, for example, of the ethenyl, propenyl, butenyl, pentenyl, hexenyl, acetylenyl, propynyl, butynyl, pentynyl and hexynyl radicals and their branched isomers. The alkyl group, within the meaning of the invention including the alkenyl and alkynyl groups, can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups or one or more aryl groups, with the alkoxy and aryl groups as defined in the context of the present invention.

The term "aryl" denotes generally an aromatic cyclic substituent comprising from 6 to 20 carbon atoms. In the context of the invention, the aryl group can be mono- or polycyclic. Mention may be made, by way of indication, of the phenyl, benzyl and naphthyl groups. The aryl group can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups or one or more alkyl groups, with the alkoxy and alkyl groups as defined in the context of the present invention.

The term "heteroaryl" denotes generally an aromatic mono- or polycyclic substituent comprising from 5 to 10 members, including at least 2 carbon atoms, and at least one heteroatom chosen from nitrogen, oxygen, boron, silicon, phosphorus or sulfur. The heteroaryl group can be mono- or polycyclic. Mention may be made, by way of indication, of the furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidinyl, pyrazinyl, triazinyl, cinnolinyl, phthalazinyl and quinazolinyl groups. The heteroaryl group can optionally be substituted by one or more hydroxyl groups, one or more alkoxy groups, one or more halogen atoms chosen from the fluorine, chlorine, bromine and iodine atoms, one or more nitro (—$NO_2$) groups, one or more nitrile (—CN) groups, one or more aryl groups or one or more alkyl groups, with the alkyl, alkoxy and aryl groups as defined in the context of the present invention.

The term "alkoxy" means an alkyl group, as defined above, bonded via an oxygen atom (—O-alkyl).

The term "heterocycle" denotes generally a saturated or unsaturated and mono- or polycyclic substituent comprising from 5 to 10 members and comprising from 1 to 4 heteroatoms chosen, independently of one another, from nitrogen, oxygen, boron, silicon, phosphorus or sulfur. Mention may be made, by way of indication, of borolane, borole, borinane, 9-borabicyclo[3.3.1]nonane (9-BBN), 1,3,2-benzodioxaborole (catecholborane or catBH), pinacolborane (pinBH) or the morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl and isothiazolidinyl substituents. The heterocycle can optionally be substituted by one or more hydroxyl groups, one or more alkoxy groups, one or more aryl groups, one or more halogen atoms chosen from the fluorine, chlorine, bromine and iodine atoms, one or more nitro (—$NO_2$) groups, one or more nitrile (—CN) groups or one or more alkyl groups, with the alkyl, alkoxy and aryl groups as defined in the context of the present invention.

Halogen atom is understood to mean an atom chosen from the fluorine, chlorine, bromine or iodine atoms.

"Silyl" group is understood to mean a group of formula [—$Si(X)_3$] in which X is chosen from a hydrogen atom, one or more halogen atoms chosen from the fluorine, chlorine, bromine or iodine atoms, one or more alkyl groups, one or more alkoxy groups, one or more siloxy groups or one or more aryl groups, with the alkyl, alkoxy and aryl groups as defined in the context of the present invention.

"Siloxy" group is understood to mean a silyl group as defined above bonded via an oxygen atom (—O—Si(X)$_3$).

"Amino" group is understood to mean a group of formula —NR$^3$R$^4$ in which:

R$^3$ and R$^4$ represent, independently of one another, a hydrogen atom, an alkyl group, an alkenyl group, an alkynyl group, an aryl group, a heteroaryl group, a heterocycle, a silyl group or a siloxy group, with the alkyl, alkenyl, alkynyl, aryl, heteroaryl, heterocycle, silyl and siloxy groups as defined in the context of the present invention; or R$^3$ and R$^4$, taken together with the nitrogen atom to which they are bonded, form a heterocycle optionally substituted by one or more hydroxyl groups, one or more alkyl groups, one or more alkoxy groups, one or more halogen atoms chosen from the fluorine, chlorine, bromine and iodine atoms, one or more nitro (—NO$_2$) groups, one or more nitrile (—CN) groups or one or more aryl groups, with the alkyl, alkoxy and aryl groups as defined in the context of the present invention.

The substituents, radicals and groups defined above can optionally comprise deuterium ($^2$H), tritium ($^3$H), $^{11}$C, $^{13}$C, $^{14}$C, $^{15}$N, $^{18}$O, $^{18}$F, $^{29}$Si, $^{30}$Si, $^{33}$S, $^{34}$S or $^{36}$S.

According to a preferred alternative form of the invention, in the oxyborane compound of formula (I) and in the hydroborane of formula (II):

R$^1$ and R$^2$ represent, independently of one another, a hydrogen atom, an alkyl group, an aryl group or an alkoxy group, said alkyl, aryl and alkoxy groups optionally being substituted, or R$^1$ and R$^2$, taken together with the boron atom to which they are bonded, form an optionally substituted heterocycle.

Preferably, in the oxyborane compound of formula (I) and in the hydroborane of formula (II):

R$^1$ and R$^2$ represent, independently of one another, a hydrogen atom, an alkyl group chosen from methyl, ethyl, propyl, butyl, pentyl, hexyl or heptyl groups or their branched isomers or the cyclohexyl group, or an aryl group chosen from benzyl or phenyl; or R$^1$ and R$^2$, taken together with the boron atom to which they are bonded, form a heterocycle, said heterocycle being chosen from catBH, pinBH or 9-BBN.

Catalyst, within the meaning of the invention, is understood to mean any compound which is capable of modifying, in particular by increasing, the rate of the chemical reaction in which it participates and which is regenerated at the end of the reaction. This definition encompasses both catalysts, that is to say compounds which exert their catalytic activity without having to be subjected to any modification or conversion, and compounds (also known as precatalysts) which are introduced into the reaction medium and which are converted therein into a catalyst.

As already indicated, in the process of the invention, the catalyst can be (i) an organic base chosen from nitrogen-comprising organic bases, phosphorus-comprising organic bases, carbon-comprising bases or oxygen-comprising organic bases, with it being possible for the nitrogen-comprising organic bases to be secondary or tertiary amines chosen, for example, from triazabicyclodecene (TBD), N-methyltriazabicyclodecene (MeTBD), 1,8-diazabicyclo-[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA), arginine or phosphazenes chosen, for example, from (tert-butylimino)tris(dimethylamino)phosphorane (P1-t-Bu), (tert-butylimino)tri(pyrrolidino)phosphorane (BTPP), tetramethyl(tris(dimethylamino)phosphoranylidene)-phosphoric triamid ethylimine (P2-Et), (tert-octylimino)tris(dimethylamino)phosphorane (P1-t-Oct) and 1-tert-butyl-4,4,4-tris(dimethylamino)-2,2-bis-[tris(dimethylamino)phosphoranylidenamino]-2λ5,4λ5-catenadi(phosphazene) (P4-Bu);

it being possible for the phosphorus-comprising organic bases to be alkyl- or arylphosphines chosen, for example, from triphenylphosphine, 2,2'-bis(diphenylphosphino)-1,1'-binaphthyl (BINAP), triisopropylphosphine, 1,2-bis(diphenylphosphino)-ethane (dppe) or tricyclohexylphosphine (PCy$_3$); alkyl- and arylphosphonates chosen, for example, from diphenyl phosphate, triphenyl phosphate (TPP), tri(isopropylphenyl) phosphate (TIPP), cresyl diphenyl phosphate (CDP) or tricresyl phosphate (TCP); alkyl and aryl phosphates chosen, for example from di(n-butyl) phosphate (DBP), tris(2-ethylhexyl) phosphate or triethyl phosphate; alkyl and aryl phosphinites and phosphonites chosen, for example, methyl diphenylphosphinite and methyl diphenylphosphonite; or azaphosphines chosen, for example, from 2,8,9-trimethyl-2,5,8,9-tetraaza-1-phosphabicyclo[3.3.3]undecane (BV$^{Me}$) and 2,8,9-triisobutyl-2,5,8,9-tetraaza-1-phosphabicyclo[3.3.3]undecane (BV$^{iBu}$;

carbon-comprising bases for which the protonation takes place on a carbon atom, such as, for example, the N-heterocyclic carbenes resulting from an imidazolium salt chosen from 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-trimethylphenyl)-1H-imidazol-3-ium, 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di(tert-butyl)-1H-imidazol-3-ium (also known as "ItBu" or "ItBu carbene" in the continuation of the account) or 1,3-di(tert-butyl)-4,5-dihydro-1H-imidazol-3-ium salts, said salts being in the form of chloride salts, for example; or oxygen-comprising bases chosen, for example, from hydrogen peroxide, benzoyl peroxide, pyridine oxide (PyO), N-methylmorpholine oxide or 1-λ$^1$-oxidanyl-2,2,6,6-tetramethylpiperidine.

Examples of N-heterocyclic carbenes are represented below:

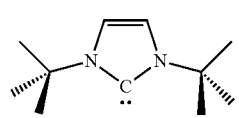

ItBu

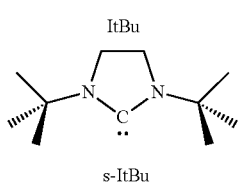

s-ItBu

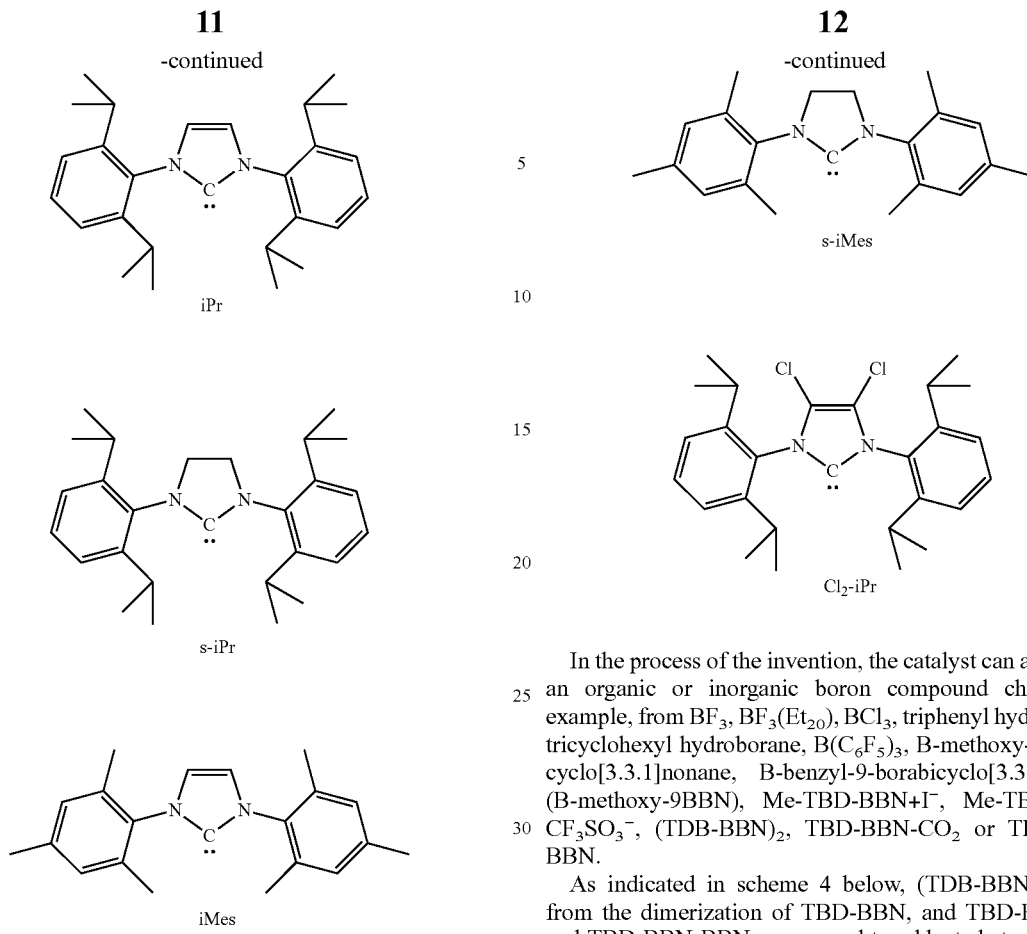

In the process of the invention, the catalyst can also be (ii) an organic or inorganic boron compound chosen, for example, from $BF_3$, $BF_3(Et_2O)$, $BCl_3$, triphenyl hydroborane, tricyclohexyl hydroborane, $B(C_6F_5)_3$, B-methoxy-9-borabicyclo[3.3.1]nonane, B-benzyl-9-borabicyclo[3.3.1]nonane (B-methoxy-9BBN), Me-TBD-BBN+I⁻, Me-TBD-BBN+ $CF_3SO_3^-$, $(TDB-BBN)_2$, $TBD-BBN-CO_2$ or TBD-BBN-BBN.

As indicated in scheme 4 below, $(TDB-BBN)_2$ results from the dimerization of TBD-BBN, and $TBD-BBN-CO_2$ and TBD-BBN-BBN correspond to adducts between TBD-BBN and $CO_2$ or 9-BBN.

Scheme 4

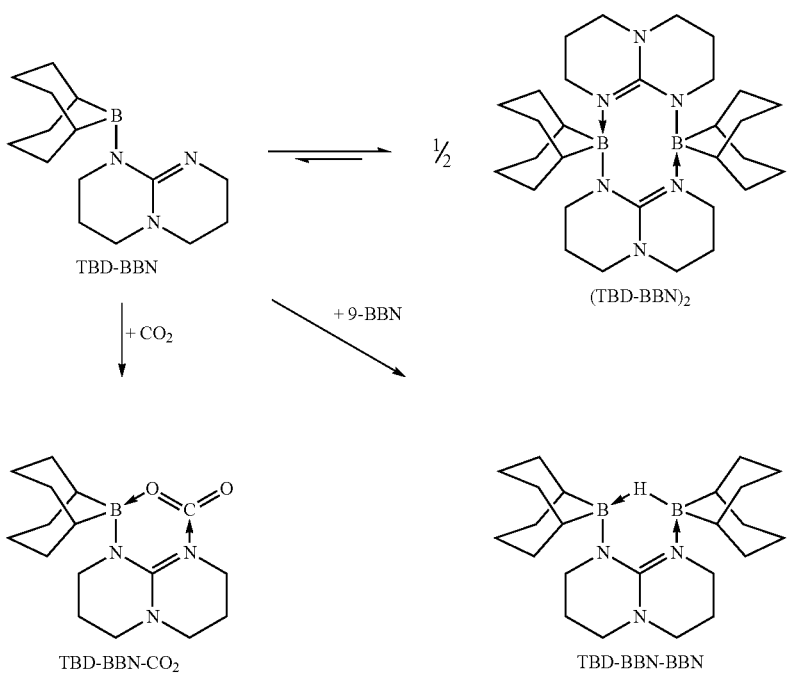

Me-TBD-BBN⁺ I⁻, (TDB-BBN)₂, TBD-BBN-CO₂ and TBD-BBN-BBN can be obtained, for example, according to the protocols described in the experimental part. Me-TBD-BBN+CF₃SO₃⁻ and also Me-TBD-BBN⁺ X⁻, in which X⁻ is chosen from fluorine, chlorine and bromine, can also be prepared by a protocol similar to that described for Me-TBD-BBN⁺ I⁻.

In the process of the invention, the catalyst can in addition be (iii) an organic or inorganic aluminum compound chosen, for example from AlCl₃, AlBr₃, aluminum isopropoxide or aluminum ethoxide.

According to a preferred alternative form of the invention, the catalyst is (i) an organic base chosen from:
 nitrogen-comprising bases, in particular triazabicyclodecene (TBD), N-methyltriazabicyclodecene (MeTBD), 1,8-diazabicyclo[5.4.0]undec-7-ene (DBU), arginine or phosphazenes chosen from (tert-butylimino)tris(dimethylamino)phosphorane (P1-t-Bu), (tert-butylimino)tri(pyrrolidino)phosphorane (BTPP), tetramethyl(tris(dimethylamino)phosphoranylidene)-phosphoric triamid ethylimine (P2-Et), (tert-octylimino)tris(dimethylamino)phosphorane (P1-t-Oct) and 1-tert-butyl-4,4,4-tris(dimethylamino)-2,2-bis-[tris(dimethylamino)phosphoranylidenamino]-2λ5,4λ5-catenadi (phosphazene) (P4-Bu);
 phosphorus-comprising bases, in particular 1,2-bis(diphenylphosphino)ethane (dppe), tricyclohexylphosphine (PCy₃), 2,8,9-trimethyl-2,5,8,9-tetraaza-1-phosphabicyclo[3.3.3]undecane (BV$^{Me}$) or 2,8,9-triisobutyl-2,5,8,9-tetraaza-1-phosphabicyclo[3.3.3]-undecane (BV$^{iBu}$);
 pyridine oxide (PyO); or
 1,3-di(tert-butyl)-1H-imidazol-3-ium or ItBu carbene.

The catalysts can, if appropriate, be immobilized on heterogeneous supports, for example, in order to provide for ready separation of said catalyst and/or its recycling. Said heterogeneous supports can be chosen from supports based on silica gel or on plastic polymers, such as, for example, polystyrene, carbon-comprising supports chosen from carbon nanotubes, silica carbide, alumina or magnesium chloride ($MgCl_2$).

In the process according to the invention, the reaction can take place under a $CO_2$ pressure, by sparging $CO_2$ into the reaction medium, or under a dry atmosphere comprising $CO_2$ (dried ambient air comprising, for example, approximately 78% by volume of nitrogen, 21% by volume of oxygen and approximately from 0.2 to 0.04% by volume of carbon dioxide). The reaction can also take place using supercritical $CO_2$.

Preferably, the reaction takes place under a $CO_2$ pressure. The pressure of the $CO_2$ can then be between 0.2 and 75 bar, preferably between 0.2 and 30 bar and more preferably between 1 and 10 bar, limits included.

The temperature of the reaction can be between 20 and 150° C., preferably between 20 and 125° C. and more preferably between 20 and 70° C., limits included.

The duration of the reaction depends on the degree of conversion of the hydroborane of formula (II) and on the nature of the oxyborane compound of formula (I) desired. The reaction can be carried out over a period of time of 5 minutes to 300 hours, advantageously of 2 minutes to 250 hours and preferably of 10 minutes to 200 hours, limits included.

The process of the invention, in particular the reaction between the various reactants, can take place in a or a mixture of at least two solvent(s) chosen from:
 ethers, preferably diethyl ether or THF;
 hydrocarbons, preferably benzene or toluene;
 nitrogenous solvents, preferably pyridine or acetonitrile;
 sulfoxides, preferably dimethyl sulfoxide;
 alkyl halides, preferably chloroform or methylene chloride.

The various reactants used in the process of the invention (the hydroboranes of formula (II), the (pre)catalysts, and the like) are generally commercial compounds or can be prepared by any process known to a person skilled in the art.

The concentration of the hydroborane of formula (II) is from 0.1 to 2 mol/l, preferably from 0.3 to 1.5 mol/1 and more preferably from 0.5 to 1.5 mol/1. This concentration is calculated on the basis of the volume of solvent introduced.

The amount of catalyst is from 0.00001 to 1 molar equivalent, preferably from 0.0001 to 0.1 molar equivalent and more preferably from 0.001 to 0.1 molar equivalent, limits included, with respect to the hydroborane of formula (II).

As indicated above, the oxyborane compounds of formula (I) prepared by the process of the invention exhibit the advantage of readily lending themselves to various types of reaction in order to result in varied chemical compounds, such as methane derivatives, in particular oxygen-comprising, halogen-comprising or amine-comprising methane derivatives, especially formic acid, formaldehyde, methanol, methane, methyl halide or methyl amine. For example, the hydrolysis of the compounds of formula (I) under conditions known to a person skilled in the art results in formic acid when Y represents —CHO, in formaldehyde when Y represents —$CH_2$—O—$BR^1R^2$, with $R^1$ and $R^2$ as defined above, and in methanol when Y represents —$CH_3$. The oxyboranes of formula (I) can also react with a hydrohalic acid chosen from HF, HCl, HBr and HI. For example, the reaction of the oxyboranes of formula (I) with HI, under conditions known to a person skilled in the art, results in methyl iodide when Y represents —$CH_3$. The methyl iodide can, in its turn, be subjected to a reaction with an amine to result in the corresponding methylamine, as shown in the Reaxys databases.

A subject matter of the invention is thus the use of the oxyborane compounds of formula (I) obtained according to the process of the invention in the preparation of methane derivatives, in particular oxygen-comprising, halogen-comprising or amine-comprising methane derivatives, especially formic acid, formaldehyde, methanol, methane, methyl halide derivatives and methyl amine derivatives.

The methane derivatives thus obtained can then be used in the manufacture of vitamins, pharmaceutical products, adhesives, acrylic fibers and synthetic leathers, pesticides and fertilizers. This constitutes another subject matter of the invention.

The invention also relates to a process for the manufacture of vitamins, pharmaceutical products, adhesives, acrylic fibers, synthetic leathers, pesticides and fertilizers comprising a stage of preparation of methane derivatives, in particular oxygen-comprising, halogen-comprising or amine-comprising methane derivatives, from oxyborane compounds obtained by the process according to the invention.

As already indicated, the process according to the invention results in the formation of oxyborane compounds with a good, indeed even excellent, yield (ranging from 50% to 100%, for example) and a good selectivity (which can reach 100% in a single type of oxyborane compound). In the case where the catalyst is supported, a simple filtration can make it possible to recover it and to remove possible boron-based by-products formed.

The process of the invention makes it possible to also prepare labelled oxyborane compounds of formula (I). This constitutes another subject matter of the invention. The labelled oxyborane compounds correspond to the oxyborane compounds of formula (I) comprising at least one chosen isotope or radiolabel/radiotracer.

Isotopes is understood to mean, for one and the same element, two atoms having the same number of protons (and of electrons) but a different number of neutrons. As they have the same number of electrons and of protons, the chemical properties of the isotopes of one and the same element are virtually identical. However, there may exist slight variations in the rate of a chemical reaction when one of the atoms of a reactant is replaced by one of its isotopes. On the other hand, as the nucleus does not comprise the same number of neutrons, the weight of the atoms varies, which may render the atom unstable: this is why they may be radioactive. They are then radioisotopes. In the context of the invention, the term "isotopes" can also encompass "radioisotopes".

Radiolabelling is the act of combining, with a given molecule or a given compound, an isotope which will make it possible to monitor the change in and/or the fixing of the molecules, for example in an organ. The radiotracer is the radioactive element(s) present within a molecule in order to monitor the course of this substance, for example in an organ.

This process can thus make possible access to labelled oxyborane compounds of formula (I) and to their reaction product. For example, the reaction between a labelled methoxyborane and hydriodic acid provides the corresponding labelled iodomethane, which is used in the synthesis of labelled methyl amines (S. C. Choudhry, L. Serico and J. Cupano, Journal of Organic Chemisty, 1989, vol. 54, pp. 3755-3757).

The use of molecules for tracing, metabolization, imaging and other purposes is described in detail in the literature (U. Pleiss and R. Voges, *Synthesis and Applications of Isotopically Labelled Compounds*, Volume 7, Wiley-VCH, 2001; R. Voges, J. R. Heys and T. Moenius, *Preparation of Compounds Labeled with Tritium and Carbon-14*, Wiley-VCH: Chippenham (UK) 2009).

The possibility of forming labelled oxyborane compounds of formula (I) can be ensured by the availability of labelled reactants which correspond, for example, by:

- hydroboranes $R^1R^2BH$ labelled with $^2H$ (D) or $^3H$ (T) are obtained by deuteration of dihydroboranes $(R^1R^2B)_2$ in the presence of molecular deuterium $D_2$ (C. S. Wei, C. A. Jimenez-Hoyos, M. F. Videa, J. F. Hartwig and M. B. Hall, *J. Am. Chem. Soc.*, 2010, 132, 3078);
- hydroboranes $R^1R^2BH$ labelled with $^2H$ (D) or $^3H$ (T) are obtained by H/D exchange in the presence of molecular deuterium $D_2$ and of hydroborane $R^1R^2BH$ (J. Y. Wu, B. Moreau and T. Ritter, *J. Am. Chem. Soc.*, 2009, 131, 12915; J. M. Farrell, J. A. Hatnean and D. W. Stephan, *J. Am. Chem. Soc.*, 2012, 134, 15728; S. Bontemps, L. Vendier and S. Sabo-Etienne, *Angew, Chem. Int. Ed.*, 2012, 51, 1671);
- hydroboranes $R^1R^2BH$ labelled with $^2H$ (D) or $^3H$ (T) are obtained by using $BH_3$(THF) as boron-comprising reactant in the synthesis of hydroborane instead of $BH_3$(THF) (J. M. Brown and G. C. Lloyd-Jones, *J. Am. Chem. Soc.*, 1994, 116, 866);
- hydroboranes $R^1R^2BH$ labelled with $^2H$ (D) or $^3H$ (T) are obtained by reacting a boron halide of formula $R^1R^2BX$ (X=F, Cl, Br or I) with a labelled metal hydride, such as lithium hydride (LiH) or lithium aluminum hydride (LiAlH$_4$) (Y. Segawa, Y. Suzuki, M. Yamashita and K. Nozaki, *J. Am. Chem. Soc.*, 2008, 130, 16069; Z. P. Lu, Z. H. Cheng, Z. X. Chen, L. H. Weng, Z. H. Li and H. D. Wang, *Angew. Chem. Int. Ed.*, 2011, 50, 12227), the hydrides both being available in deuterated and tritiated versions (T. A. Kochina, D. V. Vrazhnov, E. N. Sinotova, V. V. Avrorin, M. Y. Katsap and Y. V. Mykhov, *Russ. J. Gen. Chem.+*, 2002, 72, 1222; E. A. Shishigin, V. V. Avrorin, T. A. Kochina and E. N. Sinotova, *Russ. J. Gen. Chem.+*, 2005, 75, 152);
- $CO_2$ labelled with $^{11}C$ or $^{14}C$, which is the main source of $^{11}C$ and $^{14}C$, is obtained by acidification of labelled barium carbonate $Ba^{14}CO_3$ (R. Voges, J. R. Heys and T. Moenius, *Preparation of Compounds Labelled with Tritium and Carbon-14*, Wiley-VCH: Chippenham (UK), 2009).

According to a preferred alternative form of the invention, in the process for the preparation of labelled oxyborane compounds of formula (I), the $CO_2$ used is labelled $CO_2$ in which C represents a $^{11}C$, $^{13}C$ or $^{14}C$ isotope.

According to another preferred alternative form of the invention, in the process for the preparation of labelled oxyborane compounds of formula (I), the hydroborane used is a labelled hydroborane of formula $R^1R^2BH$ in which H represents deuterium ($^2H$) or tritium ($^3H$).

According to yet another preferred alternative form of the invention, in the process for the preparation of labelled oxyborane compounds of formula (I), the $CO_2$ and the hydroborane used are both labelled: the $CO_2$ is labelled $CO_2$ in which C represents a $^{11}C$, $^{13}C$ or $^{14}C$ isotope and the hydroborane is a labelled hydroborane of formula $R^1R^2BH$ in which H represents deuterium ($^2H$) or tritium ($^3H$).

The molecules labelled with $^{14}C$ have contributed to numerous advances in life sciences (enzymatic mechanisms, biosynthetic mechanisms, biochemistry), environmental sciences (tracing of wastes), research (elucidation of reaction mechanisms) or diagnostics, or the research and development of novel pharmaceutical and therapeutic products. This is because molecules labelled with $^{14}C$ exhibit an advantage for metabolic studies as $^{14}C$ is easily detectable and quantifiable in in vitro and in vivo medium.

The main source of $^{14}C$ is $^{14}CO_2$, which is obtained by acidification of barium carbonate $Ba^{14}CO_3$. The development of processes for the synthesis of base molecules used in the preparation of medicaments is thus essential in order to produce active principles labelled with $^{14}C$, the metabolism of which can thus be determined (R. Voges, J. Heys and T. Moenius, *Preparation of Compounds Labeled with Tritium and Carbon-14*, Wiley-VCH: Chippenham (UK), 2009).

The major constraint limiting the synthesis of molecules labelled with $^{14}C$ is the need to have a high yield of $^{14}C$ product formed with respect to the amount of $^{14}CO_2$ used and to be based on a restricted number of stages in order to limit as much as possible the costs related to the use of $Ba^{14}CO_3$ (U. Pleiss and R. Voges, *Synthesis and Applications of Isotopically Labelled Compounds, Volume 7*, Wiley-VCH, 2001; R. Voges, J. R. Heys and T. Moenius, *Preparation of Compounds Labelled with Tritium and Carbon-14*, Wiley-VCH: Chippenham (UK), 2009).

The process according to the invention meets these requirements as the $CO_2$ working pressure can be low, for example from 0.2 to 1 bar. In addition, the degree of incorporation of $CO_2$ (or yield with respect to the $CO_2$ introduced) remains high and may, for example, exceed 95%.

The temperature, reaction duration and solvent conditions and also the amounts of reactants and catalysts employed in the process for the preparation of the labelled oxyborane compounds of formula (I') are those described above in the context of the process for the preparation of the oxyborane compounds of formula (I).

A subject matter of the invention is the use of the labelled oxyborane compounds of formula (I) obtained according to the process of the invention in the preparation of labelled methane derivatives, in particular oxygen-comprising, halogen-comprising or amine-comprising methane derivatives, in particular formic acid, formaldehyde, methanol, methane, methyl halide or methyl amine.

The labelled methane derivatives thus obtained can then be used in the manufacture of vitamins, pharmaceutical products, adhesives, acrylic fibers and synthetic leathers, pesticides and fertilizers, for example. This constitutes another subject matter of the invention.

The invention also relates to a process for the manufacture of vitamins, pharmaceutical products, adhesives, acrylic fibers, synthetic leathers, pesticides and fertilizers, for example, comprising a stage of preparation of labelled methane derivatives, in particular oxygen-comprising, halogen-comprising or amine-comprising methane derivatives, from labelled oxyborane compounds of formula (I) obtained by the process according to the invention.

An additional subject matter of the invention is a process for the manufacture of tracers and radiotracers, characterized in that it comprises a stage of preparation of labelled methane derivatives, in particular oxygen-comprising, halogen-comprising or amine-comprising methane derivatives, from labelled oxyborane compounds of formula (I) obtained by the process according to the invention.

Other advantages and characteristics of the present invention will become apparent on reading the examples below, given by way of illustration and without implied limitation.

EXAMPLES

Example 1

The catalytic hydroboration reaction of $CO_2$ to give methanol, presented in scheme 5 below, was carried out according to the following experimental protocol.

The hydroborane $R^1R^2BH$ (1 equivalent), the precatalyst (0.0001 to 1 molar equivalent) and the solvent are introduced into a Schlenk tube under an inert atmosphere in a glove box, which tube is subsequently sealed with a J. Young tap. The hydroborane concentration in the reaction mixture is approximately 0.5 mol·l$^{-1}$ (concentration calculated on the basis of the volume of solvent introduced). The order of introduction of the reactants is not important.

The Schlenk tube is subsequently placed under $CO_2$ pressure (from 1 to 3 bar) using a vacuum line and is then heated at a temperature between 25 and 100° C. until the $CO_2$ has been completely converted (reaction from 5 minutes to 72 hours).

Once the reaction is complete, the resulting oxyborane compound is hydrolyzed. To this end, a volume of water equal to the volume of solvent is added with a syringe and the mixture is stirred at ambient temperature for 1 h. The volatile products are transferred, under reduced pressure, into a second Schlenk tube, resulting in an aqueous methanol solution being obtained.

The combined results are presented in table 1 below, which gives examples of conversions of $CO_2$ into methoxyborane and, after hydrolysis, its conversion into methanol.

At 20° C., the maximum TOF observed is 288 h$^{-1}$ (for $BV^{Me}$ as catalyst) and the maximum TON measured is 2014 (with $BV^{Me}$ as catalyst).

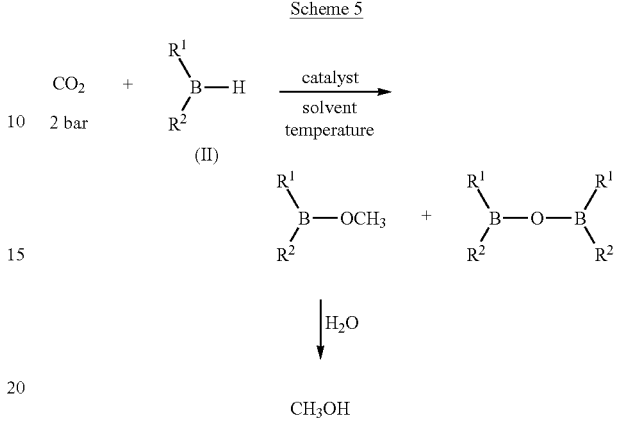

Scheme 5

Different hydroboranes, catalysts, solvents and temperatures were tested for the reaction.

The catalysts Me-TBD-BBN$^+$ I$^-$, (TDB-BBN)$_2$, TBD-BBN-$CO_2$ and TBD-BBN-BBN used in this example were prepared according to the following protocols:

Synthesis of (TBD-BBN)$_2$

A 20 ml round-bottomed flask equipped with a magnetic bar and closed with a J. Young stopper is charged with TBD (163.1 mg, 1.17 mmol, 1 eq.), dimer (9-BBN)$_2$ (143.0 mg, 0.59 mmol, 0.5 eq.) and tetrahydrofuran (3.5 ml). The round-bottomed flask is closed and the solution is stirred at 70° C. for 1 hour. The reaction mixture is cooled to ambient temperature and then the solid is filtered off on a sintered glass funnel and washed with diethyl ether. A white solid is recovered and dried under reduced pressure in order to obtain the product (TBD-BBN)$_2$ with a yield of 75% (194.9 mg).

Synthesis of TBD-BBN-$CO_2$

A 20 ml round-bottomed flask equipped with a magnetic bar and closed with a J. Young stopper is charged with (TBD-BBN)$_2$ (71.0 mg, 0.14 mmol) and tetrahydrofuran (4 ml). The reaction mixture is placed under a $CO_2$ atmosphere (1 bar). The round-bottomed flask is closed and the solution is stirred at 100° C. for 75 minutes. The white solid in the reaction mixture gradually dissolves during the heating. The reaction mixture is cooled to ambient temperature (approximately 20° C.) and then the solvent is evaporated under reduced pressure in order to recover TBD-BBN-$CO_2$ in the form of a white solid with a quantitative yield (84.0 mg).

Synthesis of TBD-BBN-BBN

A 20 ml round-bottomed flask equipped with a magnetic bar and closed with a J. Young stopper is charged with (TBD-BBN)$_2$ (100.0 mg, 0.19 mmol, 1 eq.), dimer (9-BBN)$_2$ (51.0 mg, 0.21 mmol, 1.1 eq.) and tetrahydrofuran (5 ml). The round-bottomed flask is closed and the solution is stirred at 100° C. for 150 minutes. The white solid in the reaction mixture gradually dissolves during the heating. The reaction mixture is cooled to ambient temperature and then the solvent is partially evaporated from the reaction mixture down to approximately 0.5 ml. During the evaporation of the solvent, a white solid appears. The solid is filtered off on a sintered glass funnel and washed with cold diethyl ether (−40° C.). The solid is recovered and dried under reduced pressure in order to obtain the product TBD-BBN-BBN with a yield of 76% (110.5 mg).

Synthesis of MeTBD-BBN⁺I⁻

A 20 ml round-bottomed flask equipped with a magnetic bar and closed with a J. Young stopper is charged with MeTBD (53.1 mg, 0.35 mmol, 1 eq.) and tetrahydrofuran (3.5 ml). The solution is stirred and a 1M solution of 9-iodo-9-boranicyclo[3.3.1]nonane in hexane (350 μl, 0.35 mmol, 1 eq.) is added to the reaction mixture. A white precipitate immediately forms after addition of the 9-iodo-9-boranicyclo[3.3.1]nonane solution. The round-bottomed flask is closed and the solution is stirred at ambient temperature (approximately 20° C.) for 30 minutes. The solid is filtered off on a sintered glass funnel and washed with diethyl ether. The solid is recovered and dried under reduced pressure in order to obtain the product MeTBD-BBN⁺I⁻ with a yield of 81% (112.0 mg).

according to the experimental protocol shown in example 1. The results are presented in table 2 below.

Scheme 6

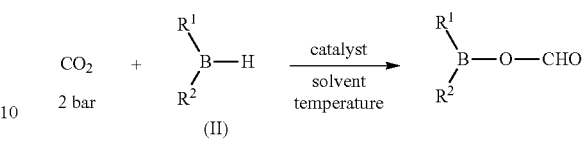

Various catalysts were also tested. In all cases, the solvent used is THF and the temperature of the reaction is 20° C.

TABLE 1

| $R^1R^2BH$ | Catalyst | Amount of catalyst (mol. eq.)* | Solvent | Temp. (° C.) | Reaction time (h) | Methoxy-borane yield (%) | Methanol yield (%) |
|---|---|---|---|---|---|---|---|
| 9-BBN | TBD | 0.025 | THF | 20 | 27 | 90 | 85 |
| 9-BBN | TBD | 0.01 | THF | 20 | 23 | 89 | 85 |
| 9-BBN | TBD | 0.001 | THF | 20 | 147 | 95 | 90 |
| 9-BBN | Me-TBD | 0.025 | THF | 20 | 7 | 93 | 87 |
| 9-BBN | Me-TBD | 0.01 | THF | 20 | 24 | 81 | 76 |
| 9-BBN | DBU | 0.025 | THF | 20 | 7 | 91 | 85 |
| 9-BBN | DBU | 0.01 | THF | 20 | 17 | 100 | 96 |
| 9-BBN | (TBD-BBN)₂ | 0.012 | THF | 20 | 166 | 80 | 75 |
| 9-BBN | TBD-BBN-CO₂ | 0.025 | THF | 20 | 7 | 66 | 63 |
| 9-BBN | TBD-BBN-BBN | 0.025 | THF | 70 | 47 | 97 | 92 |
| 9-BBN | NEt₃ | 0.025 | THF | 20 | 28 | 98 | 94 |
| 9-BBN | arginine | 0.025 | THF | 20 | 14 | 92 | 86 |
| 9-BBN | DMAP | 0.025 | THF | 70 | 42 | 95 | 89 |
| 9-BBN | dppe | 0.025 | THF | 20 | 24 | 100 | 95 |
| 9-BBN | PCy₃ | 0.025 | THF | 20 | 5 | 94 | 89 |
| 9-BBN | P1-t-Bu | 0.025 | THF | 20 | 18 | 100 | 92 |
| 9-BBN | $BV^{Me}$ | 0.025 | THF | 20 | 1 | 87 | 83 |
| 9-BBN | $BV^{Me}$ | 0.01 | THF | 20 | 3 | 95 | 90 |
| 9-BBN | $BV^{Me}$ | 0.005 | THF | 20 | 3 | 95 | 89 |
| 9-BBN | $BV^{Me}$ | 0.005 | THF | 70 | 0.4 | 94 | 89 |
| 9-BBN | $BV^{Me}$ | 0.001 | THF | 20 | 19 | 95 | 90 |
| 9-BBN | $BV^{Me}$ | 0.0001 | THF | 20 | 192 | 95 | 90 |
| 9-BBN | $BV^{Me}$ | 0.0001 | THF | 70 | 144 | 96 | 91 |
| 9-BBN | $BV^{iBu}$ | 0.025 | THF | 20 | 1 | 98 | 94 |
| 9-BBN | ItBu | 0.025 | THF | 20 | 1.5 | 90 | 86 |
| 9-BBN | ItBu | 0.025 | THF | 70 | 0.2 | 100 | 96 |
| 9-BBN | ItBu | 0.005 | THF | 70 | 0.7 | 98 | 94 |
| catBH | Me-TBD | 0.01 | THF | 20 | 163 | 98 | 93 |
| catBH | TBD-BBN-CO₂ | 0.025 | THF | 20 | 155 | 90 | 85 |
| 9-BBN | TBD | 0.025 | benzene | 20 | 170 | 97 | 92 |
| 9-BBN | TBD | 0.025 | toluene | 20 | 170 | 97 | 92 |
| 9-BBN | PyO | 0.025 | THF | 20 | 20 | 96 | 90 |
| 9-BBN | Me-TBD-BBN⁺ I⁻ | 0.025 | THF | 20 | 4 | 89 | 85 |

*The molar equivalent is understood with respect to the amount of hydroborane of formula (II).

These results show that, under the operating conditions shown in table 1, even in the presence of bulky boranes and catalysts, $CO_2$ can be converted into methoxyborane compounds with very good yields (at least 66%) and a very good selectivity. In its turn, the methoxyborane provides, after hydrolysis, methanol with very good yields (at least 63%).

Example 2

The catalytic hydroboration reaction of $CO_2$ to give formoxyborane, presented in scheme 6 below, was carried out

TABLE 2

| $R^1R^2BH$ | Catalyst | Amount of catalyst (mol. eq.)* | Reaction time (h) | Formoxyborane yield (%) |
|---|---|---|---|---|
| 9-BBN | TBD | 0.025 | 0.1 | 35 |
| 9-BBN | Me-TBD | 0.025 | 0.1 | 45 |
| 9-BBN | DBU | 0.025 | 0.1 | 32 |
| 9-BBN | NEt₃ | 0.025 | 10 | 30 |

*The molar equivalent is understood with respect to the amount of hydroborane of formula (II).

These results show that, under the operating conditions shown in table 2, $CO_2$ can be converted into formoxyborane compounds with a moderate to good yield (30 to 45%). Among the catalysts tested, Me-TBD proved to be the most effective. The formoxyborane obtained can provide, after hydrolysis, formic acid.

Example 3

The catalytic hydroboration reaction of $CO_2$ to give bis(boryl) acetal, presented in scheme 7 below, was carried out according to the experimental protocol shown in example 1. The combined results are presented below in table 3, showing examples of $CO_2$ conversions to give bis(boryl) acetal.

Scheme 7

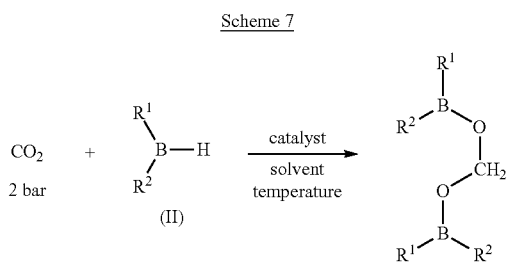

Different catalysts were also tested. In all cases, the solvent used is THF and the temperature of the reaction is 20° C.

TABLE 3

| $R^1R^2BH$ | Catalyst | Amount of catalyst (mol. eq.)* | Reaction time (h) | Bis(boryl) acetal yield (%) |
|---|---|---|---|---|
| 9-BBN | TBD | 0.025 | 0.3 | 88 |
| 9-BBN | Me-TBD | 0.025 | 0.3 | 89 |
| 9-BBN | DBU | 0.025 | 0.3 | 79 |
| 9-BBN | $NEt_3$ | 0.025 | 4.5 | 68 |

*The molar equivalent is understood with respect to the amount of hydroborane of formula (II).

These results show that, under the operating conditions shown in table 3, $CO_2$ can be converted into bis(boryl) acetal with good to excellent yields (from 68 to 89%). Among the catalysts tested, the best results were observed with triethylamine and TBD (triazabicyclodecene). Bis(boryl) acetal can provide, after hydrolysis, formaldehyde.

The abbreviations used are:

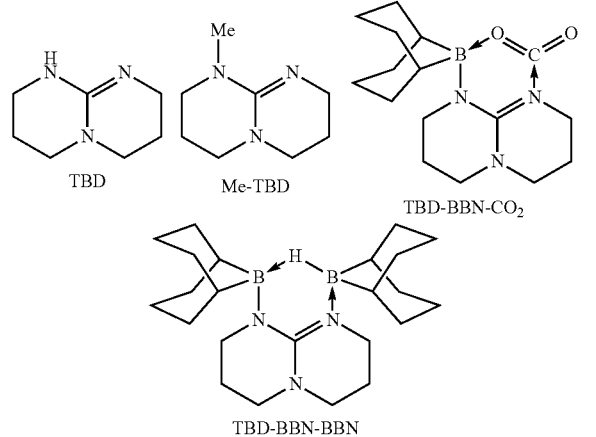

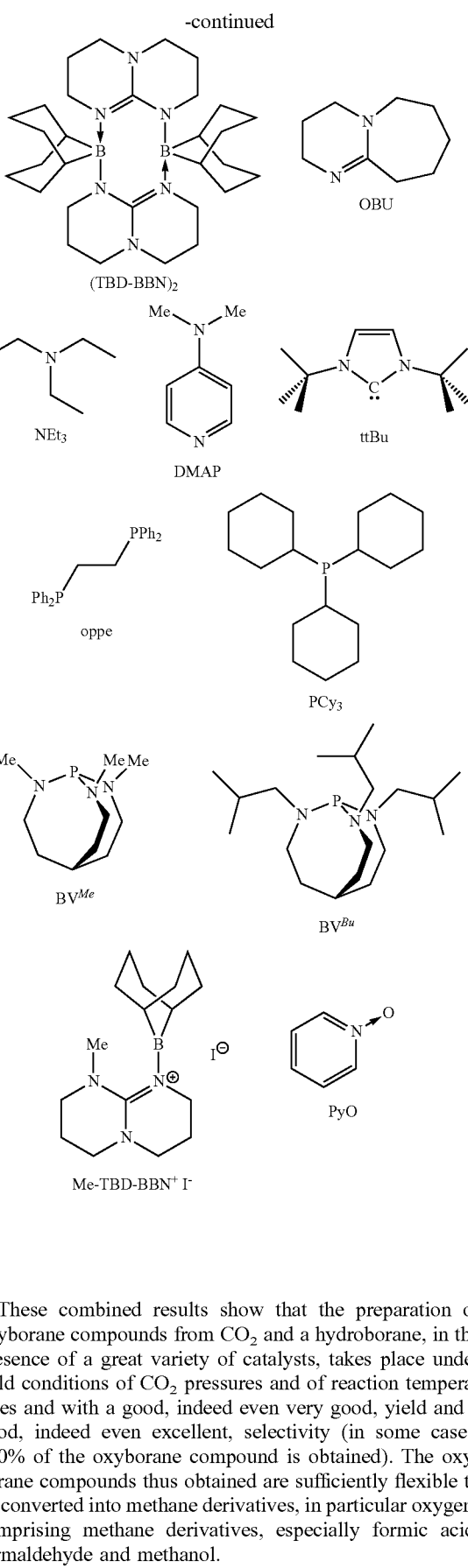

These combined results show that the preparation of oxyborane compounds from $CO_2$ and a hydroborane, in the presence of a great variety of catalysts, takes place under mild conditions of $CO_2$ pressures and of reaction temperatures and with a good, indeed even very good, yield and a good, indeed even excellent, selectivity (in some cases, 100% of the oxyborane compound is obtained). The oxyborane compounds thus obtained are sufficiently flexible to be converted into methane derivatives, in particular oxygen-comprising methane derivatives, especially formic acid, formaldehyde and methanol.

Example 4

The catalytic hydroboration reaction of $CO_2$ to give methanol, presented in scheme 5 above, was carried out according to the experimental protocol presented in example 1.

The combined results are presented in table 4 below, which gives examples of conversions of $CO_2$ to give methoxyborane and, after hydrolysis, its conversion to give methanol.

For a given catalyst, as a function of the associated hydroborane, the minimum Turn-Over Frequency (TOF) observed is from 0 h$^{-1}$ (for IMes as catalyst with catBH or pinBH as hydroborane, for example) up to a maximum TOF observed of 1.1 h$^{-1}$ (for Me-TBD as catalyst with 9-BBN as hydroborane) and the maximum Turn-Over Number (TON) measured is 8 (for Me-TBD as catalyst with 9-BBN as hydroborane).

TABLE 4

| $R^1R^2BH$ | Catalyst | Amount of catalyst (mol. eq.)* | Solvent | Temp. (° C.) | Reaction time (h) | Methoxyborane yield (%) | Methanol yield (%) |
|---|---|---|---|---|---|---|---|
| 9-BBN | TBD | 0.025 | THF | 20 | 27 | 90 | 85 |
| catBH | TBD | 0.025 | THF | 20 | 72 | 0 | 0 |
| pinBH | TBD | 0.025 | THF | 20 | 72 | 0 | 0 |
| 9-BBN | Me-TBD | 0.025 | THF | 20 | 7 | 93 | 87 |
| catBH | Me-TBD | 0.01 | THF | 20 | 163 | 98 | 93 |
| pinBH | Me-TBD | 0.025 | THF | 20 | 72 | 0 | 0 |
| 9-BBN | DBU | 0.025 | THF | 20 | 7 | 91 | 85 |
| catBH | DBU | 0.025 | THF | 20 | 0 | 0 | 0 |
| pinBH | DBU | 0.025 | THF | 20 | 0 | 0 | 0 |
| 9-BBN | IMes | 0.025 | THF | 20 | 32 | 91 | 84 |
| catBH | IMes | 0.025 | THF | 20 | 32 | 0 | 0 |
| catBH | IMes | 0.002 | THF | 20 | 32 | 0 | 0 |

These results show that the preparation of oxyborane compounds from $CO_2$ and a hydroborane, in the presence of a large variety of catalysts, requires a judicious choice between the catalyst and the associated hydroborane, taking into account in particular their respective steric hindrances, the reducing nature of the hydroborane, the nucleophilic nature of the catalyst and their solubility in the reaction medium.

The invention claimed is:

1. A process for the preparation of oxyborane compounds of formula (I):

(I)

in which:
R$^1$ and R$^2$ are, independently of one another, a hydrogen atom, a halogen atom, an alkyl group, an alkenyl group, an alkynyl group, an aryl group, a heteroaryl group, a heterocycle, a silyl group, a siloxy group, an amino group or an alkoxy group, said alkyl, alkenyl, alkynyl, aryl, heteroaryl, heterocycle, silyl, siloxy, amino and alkoxy groups optionally being substituted, or
R$^1$ and R$^2$, taken together with the boron atom to which they are bonded, form an optionally substituted heterocycle,
Y is —CHO, —CH$_2$—O—BR$^1$R$^2$, with R$^1$ and R$^2$ as defined above, or —CH$_3$,
R$^1$, R$^2$ and Y optionally comprise, independently of one another, an H, C, N, O, F, Si and/or S as defined below:
H is a hydrogen atom ($^1$H), deuterium ($^2$H) or tritium ($^3$H),
C is a carbon atom ($^{12}$C) or a $^{11}$C, $^{13}$C or $^{14}$C isotope,
N is a nitrogen atom ($^{14}$N) or a $^{15}$N isotope,
O is an oxygen atom ($^{16}$O) or an $^{18}$O isotope,
F is a fluorine atom ($^{19}$F) or a $^{18}$F isotope,
Si is a silicon atom ($^{28}$Si) or a $^{29}$Si or $^{30}$Si isotope,
S is a sulfur atom ($^{32}$S) or a $^{33}$S, $^{34}$S or $^{36}$S isotope,
consisting of adding a hydroborane of formula (II), in which R$^1$, R$^2$ and H are as defined above:

(II)

to react with $CO_2$, in which C and O are as defined above, and in the presence of a catalyst selected from the group consisting of:
(i) organic bases chosen from (a) nitrogen-organic bases chosen from triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA), or arginine or phosphazenes chosen from (tert-butylimino) tris(dimethylamino)phosphorane (P1-t-Bu), (tert-butylamino)-tri(pyrrolidino)phosphorane (BTPP), tetramethyl(tris(dimethylamino)-[phosphoranylidene)phosphoric triamid ethylimine (P2-Et), (tert-octylimino)tris(dimethylamino)phosphorane (P1-t-Oct) or 1-tert-butyl-4,4,4-tris(dimethylamino)-2,2-bis[tris(dimethylamino)phosphoranylidenamino]-2λ5,4λ5-catenadi(phosphazene) (P4-Bu);
(b) phosphorus-comprising organic bases which are alkyl- or aryl-phosphine chosen from triphenylphosphine, 2,2'-bis(diphenylphosphino)-1,1'-binaphthyl (BINAP), triisopropylphosphine, 1,2-bis(diphenylphosphino)ethane (dppe) or tricyclohexylphosphine (PCy$_3$); alkyl- or aryl-phosphonates chosen from diphenyl phosphate, triphenyl phosphate (TPP), tri(isopropylphenyl) phosphate (TIPP), cresyl diphenyl phosphate (CDP) or tricresyl phosphate (TCP); alkyl- or aryl-phosphates chosen from di(n-butyl) phosphate (DBP), tris(2-ethylhexyl) phosphate or triethyl phosphate; alkyl- or aryl-phosphinites or phosphonites chosen from methyl diphenylphosphinite or methyl diphenylphosphonite; or azaphosphines chosen from 2,8,9-trimethyl-2,5,8,9-tetraaza-1-phosphabicyclo[3.3.3]undecane (BV$^{Me}$) or 2,8,9-triisobutyl-2,5,8,9-tetraaza-1-phosphabicyclo[3.3.3]undecane (BV$^{iBu}$);

(c) carbon-comprising bases chosen from 1,3-bis(2,6-diisopropylphenyl)-1H-imidazol-3-ium, 1,3-bis(2,6-diisopropylphenyl)-4,5-dihydro-1H-imidazol-3-ium, 1,3-bis(2,4,6-trimethylphenyl)-1H-imidazol-3-ium, 1,3-bis(2,4,6-trimethylphenyl)-4,5-dihydro-1H-imidazol-3-ium, 4,5-dichloro-1,3-bis(2,6-diisopropylphenyl)-1H-imidazol-3-ium, 1,3-di(tert-butyl)-1H-imidazol-3-ium (ItBu carbine) or 1,3-di(tert-butyl)-4,5-dihydro-1H-imidazol-3-ium salts, said salts being in the form of chloride salts; or (d)

oxygen-comprising bases chosen from hydrogen peroxide, benzoyl peroxide, pyridine oxide (PyO), N-methylmorpholine oxide or 1-$\lambda^1$-oxidanyl-2,2,6,6-tetramethylpiperidine;

(ii) organic or inorganic boron compounds; and (iii) organic or inorganic aluminum compounds, wherein the catalyst is not an alkaline earth metal from Group IIA, a transition metal from Group IB to VIIIB, a rare earth metal with the atomic number of between 57 and 71; or an actinide with the atomic number of between 89 and 103.

2. The process as claimed in claim 1, wherein:

R$^1$ and R$^2$ are, independently of one another, a hydrogen atom, an alkyl group, an aryl group or an alkoxy group, said alkyl, aryl and alkoxy groups optionally being substituted, or R$^1$ and R$^2$, taken together with the boron atom to which they are bonded, form an optionally substituted heterocycle.

3. The process as claimed in claim 1, wherein:

R$^1$ and R$^2$ are, independently of one another, a hydrogen atom, an alkyl group chosen from methyl, ethyl, propyl, butyl, pentyl, hexyl or heptyl groups or their branched isomers or the cyclohexyl group, or an aryl group chosen from benzyl or phenyl; or R$^1$ and R$^2$, taken together with the boron atom to which they are bonded, form a heterocycle, said heterocycle being chosen from catecholborane (catBH), pinacolborane (pinBH) or 9-borabicyclo[3.3.1]nonane (9-BBN).

4. The process as claimed in claim 1, wherein the catalyst is (ii) an organic or inorganic boron compound chosen from BF$_3$, BF$_3$(Et$_2$O), BCl$_3$, triphenyl hydroborane, tricyclohexyl hydroborane, B(C$_6$F$_5$)$_3$, B-methoxy-9-borabicyclo[3.3.1]nonane, B-benzyl-9-borabicyclo[3.3.1]nonane (B-methoxy-9BBN), Me-TBD-BBN$^+$ I$^-$, Me-TBD-BBN$^+$ CF$_3$SO$_3^-$, (TDB-BBN)$_2$, TBD-BBN-CO$_2$ or TBD-BBN-BBN.

5. The process as claimed in claim 1, wherein, characterized in that the catalyst is (iii) an organic or inorganic aluminum compound chosen from AlCl$_3$, AlBr$_3$, aluminum isopropoxide or aluminum ethoxide.

6. The process as claimed in claim 1, wherein the catalyst is an organic base chosen from:

nitrogen-comprising bases chosen from triazabicyclodecene (TBD), N-methyltriazabicyclodecene (MeTBD), 1,8-diazabicyclo[5.4.0]undec-7-ene (DBU), or arginine or phosphazenes chosen from (tert-butylimino)-tris(dimethylamino)phosphorane (P1-t-Bu), (tert-butylimino)tri(pyrrolidino)-phosphorane (BTPP), tetramethyl(tris(dimethylamino)phosphoranylidene)phosphoric triamide ethylimine (P2-Et), (tert-octylimino)tris(dimethylamino)phosphorane (P1-t-Oct) or 1-tert-butyl-4,4,4-tris(dimethylamino)-2,2-bis[tris(dimethylamino)-phosphoranylidenamino]-2$\lambda$5,4$\lambda$5-catenadi(phosphazene) (P4-Bu);

phosphorus-comprising bases chosen from 1,2-bis(diphenylphosphino)ethane (dppe), tricyclohexylphosphine (PCy$_3$), 2,8,9 trimethyl-2,5,8,9-tetraaza-1-phosphabicyclo-[3.3.3]undecane (BV$^{Me}$) or 2,8,9-triisobutyl-2,5,8,9-tetraaza-1-phosphabicyclo[3.3.3]-undecane (BV$^{iBu}$);

pyridine oxide (PyO); or 1,3-di(tert-butyl)-1H-imidazol-3-ium (ItBu carbene).

7. The process as claimed in claim 1, wherein the reaction is carried out under a CO$_2$ pressure of between 0.2 and 75 bar.

8. The process as claimed in claim 1, wherein the reaction is carried out at a temperature of between 20 and 150° C.

9. The process as claimed in claim 1, wherein the reaction is carried out over a period of 5 minutes to 300 hours.

10. The process as claimed in claim 1, wherein the reaction is carried out in a solvent or a mixture of at least two solvent(s) chosen from:

ethers chosen from diethyl ether or THF;

hydrocarbons chosen from benzene or toluene;

nitrogenous solvents chosen from pyridine or acetonitrile;

dimethyl sulfoxide; and/or alkyl halides chosen from chloroform or methylene chloride.

11. The process as claimed in claim 1, wherein the concentration of the hydroborane of formula (II) is from 0.1 to 2 mol/l.

12. The process as claimed in claim 1, wherein the amount of catalyst is from 0.00001 to 1 molar equivalent, with respect to the hydroborane of formula (II).

13. The process as claimed in claim 1, wherein the reaction is carried out at a temperature of between 20 and 125° C.

14. The process as claimed in claim 1, wherein the reaction is carried out at a temperature of between 20 and 70° C.

15. The process as claimed in claim 1, wherein the reaction is carried out under a CO$_2$ pressure of between 0.2 and 30 bar.

16. The process as claimed in claim 1, wherein the reaction is carried out under a CO$_2$ pressure of between 1 and 10 bar.

17. The process as claimed in claim 1, wherein the reaction is carried out over a period of 2 minutes to 250 hours.

18. The process as claimed in claim 1, wherein the reaction is carried out over a period of 10 minutes to 200 hours.

19. The process as claimed in claim 1, wherein the concentration of the hydroborane of formula (II) is from 0.3 to 1.5 mol/l.

20. The process as claimed in claim 1, wherein the concentration of the hydroborane of formula (II) is from 0.5 to 1.5 mol/l.

21. The process as claimed in claim 1, wherein the amount of catalyst is from 0.0001 to 0.1 molar equivalent, with respect to the hydroborane of formula (II).

22. The process as claimed in claim 1, wherein the amount of catalyst is from 0.001 to 0.1 molar equivalent, with respect to the hydroborane of formula (II).

* * * * *